United States Patent [19]

Silver et al.

[11] Patent Number: 5,164,181

[45] Date of Patent: Nov. 17, 1992

[54] ENZYME CASTRATION OF ANIMALS

[75] Inventors: Jules Silver, Niantic, Conn.; Robert E. Hopkins, II, Scituate, Mass.

[73] Assignee: Robert E. Hopkins, II, D.V.M., Inc., Scituate, Mass.

[21] Appl. No.: 820,272

[22] Filed: Jan. 14, 1992

[51] Int. Cl.⁵ .............................................. A61K 37/54
[52] U.S. Cl. ................................ 424/94.63; 424/94.65
[58] Field of Search ........................... 424/94.63, 94.65

[56] References Cited

U.S. PATENT DOCUMENTS

| | | | |
|---|---|---|---|
| 4,156,427 | 5/1979 | Fahim | 605/54 |
| 4,339,438 | 7/1982 | Fahim | 424/643 |
| 4,356,189 | 10/1982 | Stagg et al. | 514/557 |

OTHER PUBLICATIONS

Article by Craig N. Carter, DVM, MS entitled "Pet Population Control: Another Decade Without Solutions" JA VMA, vol. 197, No. 2, Jul. 15, 1990, pp. 192-194.

Article by Donald K. Kunimitsu et al. entitled: "Chymopapain B" Methods in Enzymology, vol. XIX, Proteolytic Enzymes, edited by Gertrude E. Perlmann et al. (1970) Academic Press.

Article by Paul J. Garvin et al. entitled "Chymopapain: A Pharmacologic and Toxicologic Evaluation in Experimental Animals", Clinical Orthopaedics No. 42 (1965) J. B. Lippincott Company pp. 204-223.

Article by Ivan J. Stern, Ph.D. entitled "Biochemistry of Chymopapain", Clinical Orthopaedics and Related Research, No. 67, Nov.-Dec., 1969, pp. 42-46.

Article by Robert M. Gesler, Ph.D. entitled "Pharmacologic Properties of Chymopapain, Clinical Orthopaedics" No. 67 (1969) pp. 47-51.

*Primary Examiner*—Douglas W. Robinson
*Assistant Examiner*—Jean C. Witz
*Attorney, Agent, or Firm*—Gerstman & Ellis, Ltd.

[57] ABSTRACT

Male animals may be chemically castrated by injecting both testes and/or both spermatic cords with a castratingly effective amount of a protease enzyme such as a chymopapain-rich enzyme preparation.

21 Claims, No Drawings

ENZYME CASTRATION OF ANIMALS

BACKGROUND OF THE INVENTION

As described in a commentary on pages 192-194 of the Journal of the American Veterinary Medicine Association (JAVMA), Vol. 197, No. 2 (Jul. 15, 1990), the population growth of unwanted pets represents a significant problem in the United States.

The problem of pet overpopulation in the United States reflects a similar problem with feral dogs and cats in developing and third world nations.

As the JAVMA article describes, there are surgical methods for sterilizing dogs, cats, and other pets, but these methods are too expensive to be widely used at effective levels and have associated risks (e.g., anesthesia, infection and hemorrhage). Various products for non-surgical sterilization are currently under investigation, as indicated in the Jul. 15, 1990 article, but none have proven to be entirely satisfactory.

Also, Stagg et al. U.S. Pat. No. 4,356,189 discloses the sterilization of male animals by injection of a weak acid such as lactic acid, or a weak base, into the spermatic cords. A product based on this invention was licensed for cattle by the Food and Drug Administration/Center for Veterinary Medicine, and was being evaluated for dogs, but the license was withdrawn in August of 1990 due to evidence of non-efficacy as a result of variability in administration of the drug. Additionally, this drug was not efficacious in dogs.

Another product under development, zinc tannate, has shown promise in laboratory tests with rodents and rabbits. However, this product has yet to be tested in species intended for treatment, namely, dogs and cats. This agent is not intended for use in food production animals. See U.S. Pat. Nos. 4,156,427 and 4,339,438.

Methods used for oastration of livestock present different types of problems. The procedures are performed by non-veterinarians, and are traumatic on the animals, causing a high incidence of infection, poor growth, hemorrhage and death.

For example, about two percent of the hogs which are castrated every year develop severe disease or die from castration-associated infection. Others are sickened for a period of weeks, which causes their growth to temporarily slow. The actual number of hogs that become sick or die yearly in the United States from castration-associated infection is believed to be on the order of two million. Also, because of abscesses caused by these infections, a large portion of the carcasses or parts of carcasses cannot be used for meat.

Accordingly, there is a major need in both the field of food animal production, and in the field of pets, for an effective way to castrate animals in a manner that is safe and non-injurious to the animal, while being inexpensive as well.

In accordance with this invention an enzymic preparation is used for castration, providing reliable, effective results at low cost, and with little or no pain to the animal. Furthermore, the properly used enzyme system of this invention appear to be safe to the animal so that, for example, millions of hogs can be saved over a period of a very few years by simply using the invention of this application rather than conventional castration. It is expected that similar savings will be found in other kinds of farm animals.

Also, the use of this invention is so simple that it can be used on pets in a widespread manner for the reliable control of pet populations.

DESCRIPTION OF THE INVENTION

This invention relates to a method of chemically castrating male animals, which method comprises injecting into both testes or into both spermatio cords a castratingly effective amount of a protease enzyme preparation which is substantially free of collagenas activity.

The phrase "substantially free of collagenase activity" identifies protease enzymes that either preferentially attack non-collagen proteins, or which are largely inactive to collagen, to such an extent that the testes may be injected, to cause substantial protease activity within the testes, while the collagen outer tunic of the testes remains intact to essentially localize and contain the enzym within the testes. It is understood that small amounts of collagenas activity may be present in the enzyme, as long as the enzyme used, under the conditions of use, does not effectively break down the outer collagen membrane of the testes to permit substantial and toxic release of the enzyme into the body of the animal.

Chymopapain has been found to be particularly useful for the purpose of castration because, while the chymopapain attacks membrane proteins in the reproductive (sperm producing) cell layer in the testes to collapse the associated structures therein and to sterilize the animal, the non-cellular collagen connective tissue and outer tunic is not strongly attacked by chymopapain. Thus, the collagen outer tunic stays intact, having the effect of isolating the enzyme in the testes. It is of course desirable to isolate the enzyme in the testes, restricting free chymopapain or other enzyme to the testes, or target site. A spontaneous localization of the chymopapain typically takes place in the testes, so that damage outside of the testes does not have to occur when this invention is properly used.

Other examples of protease enzymes which are candidates for use in this invention include serine proteinases such as chymotrypsin, trypsin, or subtilisin; or cysteine proteinases such as papain, fucin, or bromelain.

Thus, animals may be sterilized by single injections into the testes. Also, sterilization may be effected by an injection into the spermatic cords to collapse the epididymis and/or the vas deferens, having an effect rather like of a vasectomy. The animal in this manner retains more male characteristics, but is sterilized. Also, there is a possibility of reversal of the sterilization procedure if the enzyme has been applied only to the vas deferens.

The enzyme may be applied to any desired animal, particularly mammals of very young age, such as dogs, cats, hogs, sheep, goats, cattle, horses, and the like Many types of proteases from microbial, plant or animal organs are known to possess an enzyme activity which would be more highly destructive to loosely arrayed cell membrane proteins versus densely arrayed connective tissue matrices commonly known as collagen.

The enzyme preparation of this invention may be conventionally buffered at a pH of about 7.2 to 8.2. Biocompatible buffers such as phosphate, imidazole, tris (hydroxy methyl) aminomethane or the like may be used. Typically, the pain of the injection to the animal is greatly reduced by maintaining the pH of an enzyme preparation similar to the tissues of the body. Additionally, or alternatively, the enzyme preparation may comprise an effective concentration of a local anesthetic such as lidocaine, carbocaine, buipivacaine or the like. Specifically, the enzyme preparation may contain about 0.1 to 4 weight percent of such local anesthetic in order to provide a effective dosage thereof.

The enzyme preparation of this invention may comprise a chymopapain activity-stabilizing amount of ethylenediamine tetraacetic acid (EDTA) and/or cysteine, both of which serve as enzyme preservatives and activators. For example, cysteine hydrochloride may be present in the enzyme preparation at a concentration of about 0.1 to 5000 millimoles per liter. EDTA may be present in about a concentration of 0.01-40 millimoles per liter, although for both of these materials other concentrations may be used where appropriate.

Other sulfhydryl containing enzyme stabilizing agents such as glutathione, methionine, or other known substances may act as equivalents to cysteine.

Other chelating agents such as disodium versenate may also stabilize chymopapain enzyme activity.

Additionally, the enzyme preparation may include a fluorescent marker material in an effective concentration to be detectible in the urine of the animal, in the event that the enzyme preparation escapes from the region of the testes. This serves as an indicator that some enzyme escape has taken place, so that the animal may be observed. For example, quinacrine hydrochloride in a concentration of about 0.2 to 20 mg. per ml. of enzyme preparation may be used. Preferably, about 0.5 mg. per ml. of quinacrine hydrochloride may be used. Additionally, other non-toxic fluorescent markers may be used for the same purpose.

Additionally, the enzyme preparation of this invention may contain a vasoconstrictor in sufficient concentration to cause constriction of precapillary arterioles in the testes upon injection of the enzyme preparation therein, to further inhibit migration of the enzyme from the testes. Typically, a vasoconstrictor such as epinephrine ma be present in the enzyme preparation in a concentration of about 0.0005 to 0.1 percent by weight.

It may be desired to inject at least a portion of the enzym preparation into the epididymis of the testes. This procedure hastens sterilization by attacking the most mature sperm cells.

Chymopapain-rich enzyme preparations are well known and commercially available. Typically, ultrapure chymopapain preparations are not necessary for use in this invention, but may be used if desired. The presence of other enzymes and the like does not necessarily render the invention ineffective as long as side effects from the enzyme activity and/or impurities are minimal.

The effective dose of the chymopapain-rich enzyme preparation depends of course on the type of animal and the size of the testes. The particular dosage in terms of enzyme activity to be used in any individual situation can be easily determined by simple experimentation using laboratory and animal testing methods.

For example, testes from dogs and cats can be removed surgically and preserved on ice for periods of hours. Enzyme preparations can then be injected into the testes, after which they are incubated in a sealed container at 32° to 37° C. in a water bath. After four hours, the testes can be removed and the degree of tissue changed and/or amount of enzyme activity remaining can be assessed. By this testing method, untreated control testes demonstrate normal tissue structure and live sperm after four hours of incubation. Such testing may be used to show how much enzyme activity and by what method significant tissue changes which might lead to sterilization are produced. Following pilot testing vitro, actual animal testing can be performed.

For example, piglets, which have testes about the size of small to medium size adult dogs, may be treated with a total of approximately 150-300 units of protease enzyme activity, into each testis, and other animals may typically be treated with proportional amounts of enzyme activity by injection into the testes, depending upon the mass of the testes. The units used here and below are well-known BAPNA units.

The chymopapain may be extracted from papaya latex in a manner similar to that described especially pages 246 and 247 of an article entitled Chymopapain B by Donald K. Kunimitsu et al. from Methods in Enzymology, Volume XIX, Proteolytic Enzymes, edited by Gertrude E. Perlmann et al. (1970) Academic Press. The purification method for the chymopapain is generally believed to be non-critical, being subject primarily to the constraints of enzyme activity and low toxicity so that the product is safe and effective.

The enzyme preparation for parenteral use must be sterilized in a conventional manner, making use for example of technology similar to the chymopapain injectable product used for treatment of prolapsed spinal disks. See for example the article by Paul J. Garvin et al. entitled Chymopapain: A Pharmacologic and Toxicologic Evaluation in Experimental Animals, pages 204-223, "Clinical Orthopaedics" No. 42 (1965) J. B. Lippincott Company.

The enzyme preparation may be encapsulated in microspheres or a microvesicle to promote slow release into the testes and containment in the testes, if desired, with the microcapsules or microvesicle being implanted in the testes.

Thus the enzyme preparation and the method of use thereof provides a significant improvement in, particularly, the enzyme castration of animals for ease of operation, low cost, and safety, so that a higher percentage of the animals avoid negative side effects from the process than in surgical castration.

The above disclosure, and the example below, have been offered for illustrative purposes only, and are not intended to limit the scope of the invention of this application, which is as defined in the claims below.

EXAMPLE 1

A complete formulation believed to optimally provide the advantages of this invention is a chymopapain rich enzyme solution having 150-250 units of enzyme activity per ml., a pH of 7.2 to 8.2, from 135 to 155 meq/L of sodium ion, from 135-155 meq/L of chloride ion, millimole per liter of ethylenediamine tetraacetic acid, 10 millimoles per liter of cysteine HCl, 0.2 percent (W/V) of lidocaine HCl, 0.001 percent (W/V) epinephrine, 0.05 percent (W/V) of quinacrine HCl, and sterile water q.s..

Such an enzyme formulation may be injected into the testicles of any desired male mammal in the manner described above to achieve sterilization

EXAMPLE 2

Four Duroc-cross, male piglets approximately nine weeks of age (weaned) were injected in the testicles with three doses of enzyme preparation. The doses selected were 1X, 2X and 3X of a minimum clinical dose determined from in vitro studies. The piglets ranged from 10.0 to 16.0 kg in weight. The objective of the study was to demonstrate any changes in testicular tissue which would result from these enzyme doses.

These piglets were anesthetized with ketamine HCl and acepromazine maleate, and were given injections as follows:

| Piglet No. | Description of Dose |
| --- | --- |
| 1R | 180 units of enzyme activity in 1.0 ml. of volume (qs with saline) into each testis. |
| 2R | 150 units of enzyme activity in 1.0 ml. of volume (qs with saline) into each testis. |
| 1L | 180 units of enzyme activity in 1.0 ml. of volume (qs with saline) into each testis. |
| 2L | 270 units of enzyme activity in 1.0 ml. of volume into each testis. |

Injection doses were based upon estimates of the testicular sizes of the piglets, being approximately 3 to 4 grams in weight per testis. By calculation it was intended to administer approximately 30, 60 or 90 units of enzyme activity per gram of testis to each testis. The total body doses of enzyme activity were 9 to 27 units of enzyme per kg of body weight. These amounts were well within known safety margins.

Treatment Results

The testes of all piglets became turgid upon injection, and remained in this condition for approximately 36 hours. Several of the animals also appeared to have cyanotic testes. The piglets all recovered uneventfully from anesthesia and showed no signs of sensitivity on palpation, anorexia, or abnormal gait. Food intake was normal for 45 days during which period the piglets averaged 0.45 to 0.60 pounds of gain per day. The piglets were turned out into a pasture where they were inadvertently exposed to two days of near freezing weather. All piglets developed pneumonia and were brought back to the barn for antibiotic treatment and care. Between Sept. 18 and Oct. 5, three piglets died. Necropsies on Piglets 2R and 1L confirmed death due to acute pneumonia. Changes in the testicular tissues included absence of the germinal layer of the seminiferous tubules. The third piglet which died was not autopsied. Th remaining piglet has been allowed to grow to slaughter weight, for future testing.

Multiple (step) sections of Piglets 2R and 1L show a total absence of spermatogenesis. The seminiferous tubules were filled with a connective tissue lattice. This finding was considered unrelated to the animals' deaths due to acute pneumonia.

Results of this study suggest that doses of 30 to 90 units of enzyme activity can be administered safely to piglets and produce degeneration of the germinal layer of the seminiferous tubules, to produce sterility.

EXAMPLE 3

Three groups of five rats each were injected with non-catalyzed suspensions of three different enzyme preparations. The left testis was used for test injections and the right testis received saline (control) injections. The objective of the study was to comparatively evaluate the action of enzyme with the action of a physiological solution.

Rats weighing 227 to 261 g were manually restrained and injected with the following enzyme preparations:

| Group | Description of Dose |
| --- | --- |
| A-1 | 162 units of papain in saline in 0.25 ml. volume (left testis); 0.25 ml. saline (right testis). |
| A-2 | 163 units of chymopapain in saline in 0.25 ml. (left testis); 0.25 ml. saline (right testis). |
| A-3 | 500 units technical grade papain in 0.25 ml. (left testis); 0.25 ml. saline (right testis). |

The enzyme preparations were not catalyzed so that more of the basic effects of the proteins could be studied versus effects from the enzyme activity, or aditives.

Treatment Results

The enzyme treated animals showed no signs of toxicity acutely or after 25 days. Testes treated with enzyme preparations showed variable enlargement followed by shrinkage when the testes wer palpated. Control testes were considered normal in size and texture. Histopathological evaluation of testes for all animals showed fibrosis and scarring of the treated testis and normal spermatic genesis in the untreated testis for all animals among the three enzyme treated groups.

It was concluded that even though enzyme activity was not maximized by catalytic additives, the action on the testis was of a type which could cause sterility (i.e., cessation of spermatogenesis). Catalyzed enzyme would of course exhibit greater enzyme activity.

That which is claimed is:

1. A method of chemically castrating male animals which comprises injecting into the testes or into the spermatic cords a castratingly effective amount of a protease enzyme preparation which does not effectively break down the outer collagen membrane of the testes to permit substantial and toxic release of the enzyme into the body of the animal and which is substantially free of collagenase activity.

2. A method of chemically castrating male animals which comprises injecting into the testes or into the spermatic cord a castratinly effective amount of a protease enzyme preparation which does not effectively break down the outer collagen membrane of the testes to permit substantial and toxic release of the enzyme into the body of the animal and which comprises chymopapain.

3. The method of claim 2 in which said enzyme preparation has a buffered pH of about 7.2 to 8.2.

4. The method of claim 2 in which said enzyme preparation comprises a chymopapain activity-stabilizing amount of EDTA and cysteine.

5. The method of claim 2 in which said enzyme preparation comprises a fluorescent marker material in effective concentration to be detactable in the animal's urine if the enzyme preparation escapes from the region of the testes.

6. The method of claim 2 in which said enzyme preparation comprises an effective concentration of a loca anesthetic.

7. The method of claim 2 in which said enzyme preparation comprises a vasoconstrictor in sufficient concentration to cause constriction of precapillary arterioles in the testes upon injection of said preparation into the testes, whereby migration of said enzyme from the testes is further inhibited.

8. The method of claim 7 in which said vasoconstrictor comprises epinephrine.

9. The method of claim 2 in which at least a portion of said enzyme preparation is injected into the epididymis of the testes.

10. The method of claim 2 in which said enzyme preparation comprises a chymopapain activity-stabilizing amount of EDTA and cysteine, said enzyme preparation also comprising a vasoconstrictor in sufficient concentration to cause constriction of precapillary arterioles in the testes upon injection of said preparation into the testes, whereby migration of said enzyme from the testes is inhibited.

11. The method of claim 10 in which said enzyme preparation has a buffered pH of about 7.2 to 8.2.

12. The method of claim in which said enzyme preparation comprises a fluorescent marker material in effective concentration to be detectable in the animals's urine if the enzyme preparation escapes from the region of the testes.

13. The method of claim 12 in which said enzyme preparation comprises an effective concentration of a local anesthetic.

14. The method of claim 13 in which said vasoconstrictor comprises epinephrine.

15. An injectable preparation which comprises a pharmaceutically acceptable, aqueous suspension of essentially 150 to 400 units per ml. of a protease enzyme preparation which does not effectively break down the outer collagen membrane of the testes to permit substantial and toxic release of the enzyme into the body of the animal and substantially free of collagenase activity, and a vasoconstrictor in sufficient concentration to cause constriction of nearby precapillary arterioles upon injection of said preparation into an animal in a clinically effective amount.

16. The preparation of claim 15 in which said protease enzyme preparation comprises chymopapain.

17. The preparation of claim 16 which comprises from 0.2 to 20 mg. of a fluorescent marker material per ml. of said preparation, to be detectable in the urine of an animal after injection of said preparation if the enzyme preparation escapes from the region of injection.

18. The preparation of claim 16 which comprises an effective concentration of a local anesthetic when a castratingly effective amount of such preparation is injected into a testicle.

19. The preparation of claim 16 in which said vasoconstrictor comprises epinephrine.

20. The preparation of claim 16 which comprises a chymopapain activity-stabilizing amount of EDTA and cysteine.

21. The preparation of claim 16 which has a buffered pH of about 7.2 to 8.2.

* * * * *